United States Patent
Miyao et al.

(10) Patent No.: US 9,605,356 B2
(45) Date of Patent: Mar. 28, 2017

(54) METHOD FOR SELECTING POLYCRYSTALLINE SILICON ROD, AND METHOD FOR PRODUCING SINGLE CRYSTALLINE SILICON

(75) Inventors: Shuichi Miyao, Niigata (JP); Junichi Okada, Niigata (JP); Shigeyoshi Netsu, Niigata (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 659 days.

(21) Appl. No.: 14/111,597

(22) PCT Filed: Apr. 4, 2012

(86) PCT No.: PCT/JP2012/002361
§ 371 (c)(1),
(2), (4) Date: Oct. 14, 2013

(87) PCT Pub. No.: WO2012/164803
PCT Pub. Date: Dec. 6, 2012

(65) Prior Publication Data
US 2014/0033966 A1     Feb. 6, 2014

(30) Foreign Application Priority Data
Jun. 2, 2011   (JP) .................. 2011-124439

(51) Int. Cl.
*C30B 13/00*    (2006.01)
*C30B 29/06*    (2006.01)
(Continued)

(52) U.S. Cl.
CPC ............ *C30B 13/00* (2013.01); *C01B 33/035* (2013.01); *C30B 15/00* (2013.01); *C30B 29/06* (2013.01);
(Continued)

(58) Field of Classification Search
CPC ....... C01B 33/035; C30B 13/00; C30B 15/00; C30B 29/06; C30B 35/007; G01N 23/207
See application file for complete search history.

(56) References Cited

U.S. PATENT DOCUMENTS

| 5,976,481 A | 11/1999 | Kubota et al. |
| 2006/0211218 A1 | 9/2006 | Boyle et al. |

(Continued)

FOREIGN PATENT DOCUMENTS

| DE | 10 2007 047 210 A1 | 4/2009 |
| EP | 1 992 593 A2 | 11/2008 |

(Continued)

OTHER PUBLICATIONS

International Search Report Issued Jun. 19, 2012 in PCT/JP12/002361 Filed Apr. 4, 2012.

(Continued)

*Primary Examiner* — Michael Kornakov
*Assistant Examiner* — Hua Qi
(74) *Attorney, Agent, or Firm* — Oblon, McClelland, Maier & Neustadt, L.L.P.

(57) ABSTRACT

Plate-like samples each having as a principal plane thereof a cross section perpendicular to the long axis direction of a polycrystalline silicon rod grown by the deposition using a chemical vapor deposition method are sampled; an X-ray diffraction measurement is performed omnidirectionally in the plane of each of the plate-like samples thus sampled; and when none of the plate-like samples has any X-ray diffraction peak with a diffraction intensity deviating from the average value ±2×standard deviation (μ±2σ) found for any one of the Miller indices <111>, <220>, <311> and <400>, the polycrystalline silicon rod is selected as the raw material for use in the production of single-crystalline silicon. The use of such a polycrystalline silicon raw material suppresses (Continued)

the local occurrence of the portions remaining unmelted, and can contribute to the stable production of single-crystalline silicon.

8 Claims, 7 Drawing Sheets

(51) Int. Cl.
    *C01B 33/035* (2006.01)
    *C30B 35/00* (2006.01)
    *C30B 15/00* (2006.01)
    *G01N 23/207* (2006.01)

(52) U.S. Cl.
    CPC ......... *C30B 35/007* (2013.01); *G01N 23/207* (2013.01)

(56) References Cited

U.S. PATENT DOCUMENTS

| | | |
|---|---|---|
| 2008/0152805 A1 | 6/2008 | Boyle et al. |
| 2008/0286550 A1 | 11/2008 | Sofin et al. |
| 2010/0009123 A1 | 1/2010 | Boyle et al. |
| 2010/0077897 A1* | 4/2010 | Gurley .................. B28D 5/024 83/451 |
| 2010/0219380 A1 | 9/2010 | Hertlein et al. |

FOREIGN PATENT DOCUMENTS

| | | |
|---|---|---|
| JP | 37 18861 | 1/1961 |
| JP | 2006 89353 | 4/2006 |
| JP | 2007-240192 A | 9/2007 |
| JP | 2010 540395 | 12/2010 |
| WO | 97 44277 | 11/1997 |

OTHER PUBLICATIONS

Extended European Search Report issued Sep. 4, 2014 in Patent Application No. 12791960.3.

* cited by examiner

120mm

10mm (a)          (b)

METHOD FOR SELECTING POLYCRYSTALLINE SILICON ROD, AND METHOD FOR PRODUCING SINGLE CRYSTALLINE SILICON

CROSS REFERENCE TO RELATED APPLICATIONS

The present application is a 35 U.S.C. §371 national stage patent application of International patent application PCT/JP2012/002361, filed on Apr. 4, 2012, published as WO/2012/164803 on Dec. 6, 2012, the text of which is incorporated by reference, and claims the benefit of the filing date of Japanese application no. 2011-124439, filed on Jun. 2, 2011, the text of which is also incorporated by reference.

TECHNICAL FIELD

The present invention relates to a method for selecting a polycrystalline silicon rod to be used as a raw material for use in the production of single-crystalline silicon, and more specifically relates to a method for selecting a non-oriented polycrystalline silicon rod suitable for stably producing single-crystalline silicon.

BACKGROUND ART

Single-crystalline silicon essential for the production of devices such as semiconductor devices is grown as a crystal by the CZ method and the FZ method, and a polycrystalline silicon rod or a polycrystalline silicon block is used as the raw materials in such a case. Such a polycrystalline silicon material is produced in many cases by the Siemens method (see, for example, Patent Literature 1). The Siemens method is a method in which by bringing a gas of a silane raw material such as trichlorosilane or monosilane into contact with a heated silicon core wire, polycrystalline silicon is grown in the vapor phase (deposited) on the surface of the silicon core wire by the CVD (Chemical Vapor Deposition) method.

For example, when single-crystalline silicon is crystal-grown by the CZ method, a polycrystalline silicon block is charged in a quartz crucible and heated to be melted, a seed crystal is dipped in the resulting silicon melt to extinguish dislocation lines to be made free from dislocation, and then the crystal pulling up is performed while the crystal diameter is being slowly expanded until the diameter of the crystal reaches a predetermined diameter. In this case, when unmelted polycrystalline silicon remains in the silicon melt, the unmelted polycrystalline pieces drift in the vicinity of the solid-liquid interface by convection to induce the generation of dislocation, and thus the polycrystalline silicon remaining unmelted causes the crystal line to be extinguished.

CITATION LIST

Patent Literature

Patent Literature 1: Japanese Patent Publication No. 37-18861

SUMMARY OF INVENTION

Technical Problem

The present inventors have obtained, in the course of the investigation of the quality improvement of polycrystalline silicon for the purpose of stably performing the production of single-crystalline silicon, findings such that, depending on the conditions at the time of the deposition of polycrystalline silicon, differences occur in the randomness of the orientation of the crystal grains in the polycrystalline silicon rod. In contrast to single-crystalline silicon, a polycrystalline silicon block includes a large number of crystal grains, and such a large number of crystal grains tend to be regarded as independently randomly oriented. However, according to the investigation performed by the present inventors, the crystal grains included in a polycrystalline silicon block are not necessarily completely randomly oriented.

In a powder sample obtained by pulverizing a polycrystalline silicon block, the individual crystal grains can be handled as completely randomly oriented. In fact, in an X-ray diffraction measurement performed with a powder sample, even when the powder sample is rotated arbitrarily in relation to the incident X-ray, no change is found in the chart obtained.

On the contrary, according to the results of the X-ray diffraction measurement performed by the present inventors by sampling plate-like samples, each having as a principal plane thereof a cross section perpendicular to the long axis direction of a polycrystalline silicon rod, from many different polycrystalline silicon rods grown by the deposition using a chemical vapor deposition method, and by performing X-ray diffraction measurement omnidirectionally in the plane of each of the plate-like samples, it has been revealed that a remarkable dependence on the X-ray incident direction is sometimes found in the diffraction intensity of any of the X-ray diffraction peaks from the crystal planes having the Miller indices of <111>, <220>, <311> and <400>.

Such a remarkable dependence on the X-ray incident direction means that the crystal grains included in the polycrystalline silicon block are not randomly oriented, and the crystal grains tend to align in the direction of the crystal plane having a specific Miller index.

It has also been revealed that when a polycrystalline silicon rod or a polycrystalline silicon block including crystal grains oriented in the direction of the crystal plane having a specific Miller index is used as a raw material for use in the production of single-crystalline silicon, portions remaining unmelted are sometimes locally caused, and such portions remaining unmelted induce the occurrence of the dislocations and can be a cause for the extinguishment of the crystal line.

The present invention has been achieved on the basis of a novel finding that differences are caused in the orientation randomness of the crystal grains in the polycrystalline silicon depending on the various conditions at the time of the deposition in the growth of the polycrystalline silicon rod by using a chemical vapor deposition method; and an object of the present invention is to provide a polycrystalline silicon material having a high random orientation property, namely, a non-oriented polycrystalline silicon rod and a non-oriented polycrystalline silicon block so as to contribute to the stable production of single-crystalline silicon.

Solution to Problem

In order to solve the foregoing technical problem, the method for selecting a polycrystalline silicon rod according to the present invention is a method for selecting a polycrystalline silicon rod to be used as a raw material for use in the production of single-crystalline silicon, wherein the polycrystalline silicon rod is a product grown by the deposition using a chemical vapor deposition method; and plate-like samples each having as a principal plane thereof a cross section perpendicular to the long axis direction of the polycrystalline silicon rod are sampled; an X-ray diffraction measurement is performed omnidirectionally in the plane of each of the plate-like samples; and when none of the plate-like samples has any X-ray diffraction peak with a diffraction intensity deviating from the average value ±2×standard deviation ($\mu \pm 2\sigma$) found for any one of the Miller indices <111>, <220>, <311> and <400>, the polycrystalline silicon rod is selected as the raw material for use in the production of single-crystalline silicon.

The polycrystalline silicon rod thus selected or the polycrystalline silicon block obtained by pulverizing the polycrystalline silicon rod thus selected for any one of the Miller indices <111>, <220>, <311> and <400> is polycrystalline silicon having an orientation property such that no X-ray diffraction peak having a diffraction intensity deviating from the average value ±2×standard deviation ($\mu \pm 2\sigma$) is shown; and in the method for producing single-crystalline silicon according to the present invention, the polycrystalline silicon rod thus selected or the polycrystalline silicon block obtained by pulverizing the polycrystalline silicon rod thus selected is used as a raw material for use in the production of single-crystalline silicon.

Advantageous Effects of Invention

The crystal growth performed with the polycrystalline silicon rod according to the present invention by the FZ method, or the crystal growth performed by the CZ method with the polycrystalline silicon block obtained by crushing the polycrystalline silicon rod suppresses the local occurrence of the portions remaining unmelted, and can contribute to the stable production of single-crystalline silicon.

DESCRIPTION OF EMBODIMENTS

Hereinafter, the embodiments of the present invention are described with reference to the accompanying drawings.

Figure 1A:
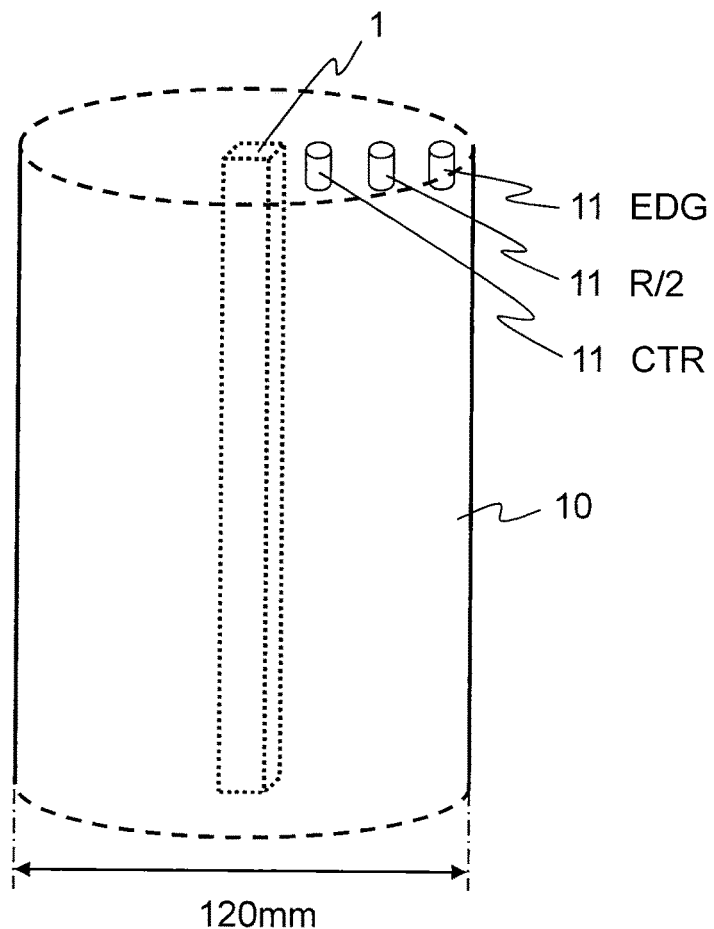
FIG. 1A is a diagram for illustrating an example of the sampling of a plate-like sample for use in an X-ray diffraction measurement from a polycrystalline silicon rod grown by the deposition using a chemical vapor deposition method.
Figure 1B:
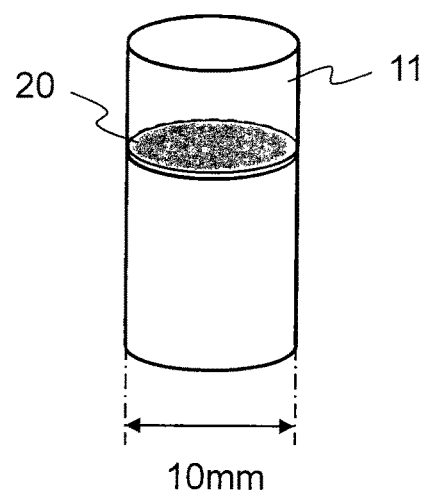
FIG. 1B is another diagram for illustrating an example of the sampling of a plate-like sample for use in an X-ray diffraction measurement from a polycrystalline silicon rod grown by the deposition using a chemical vapor deposition method.

FIG. 1A and FIG. 1B are the diagrams for illustrating the example of the sampling of the plate-like sample 20 for use in the X-ray diffraction profile measurement from the polycrystalline silicon rod 10 grown by the deposition using a chemical vapor deposition method such as the Siemens method. In FIG. 1, the reference sign 1 represents a silicon core wire used for forming the silicon rod by depositing polycrystalline silicon on the surface of the silicon core wire. In this example, for the purpose of verifying the occurrence of the radial direction dependence of the non-orientation property of the polycrystalline silicon rod, plate-like samples 20 are sampled from three different portions (CTR: portion close to silicon core wire 1, EDG: portion close to side surface of polycrystalline silicon rod 10, R/2: portion midway between CTR and EGD); however, the sampling is not limited to the sampling from such portions.

The diameter of the polycrystalline silicon rod 10 illustrated in FIG. 1A is nearly 120 mm, and rods 11 of nearly 10 mm in diameter and nearly 60 mm in length are gouged out in parallel to the silicon core wire 10 from the three portions (CTR: portion close to silicon core wire 1, EDG: portion close to side surface of polycrystalline silicon rod 10, R/2: portion midway between CTR and EGD) located from the side of the silicon core wire 1 to the side surface of the polycrystalline silicon rod 10. Then, as shown in FIG. 1B, from each of the rods 11, a plate-like sample 20 having as a principal plane thereof a cross section perpendicular to the long axis direction of the rod 11 is sampled in a thickness of nearly 2 mm.

The case where the portions from which the rods 11 are sampled are the foregoing three portions satisfactorily represents the properties of the whole of the silicon rod 10; however, the sampled portions depend on the diameter of the silicon rod 10 or the diameters of the gouged rods 11, and hence the sampling is not required to be limited to the foregoing case, and may be performed from any portions as long as the properties of the whole of the silicon rod 10 can be rationally estimated. The length of each of the rods 11 may be appropriately determined in consideration of the factors such as workability. Further, the plate-like sample 20 may be sampled from any portion of each of the gouged rods 11.

The method for sampling the plate-like sample 20 is also not particularly limited.

Figure 1C:
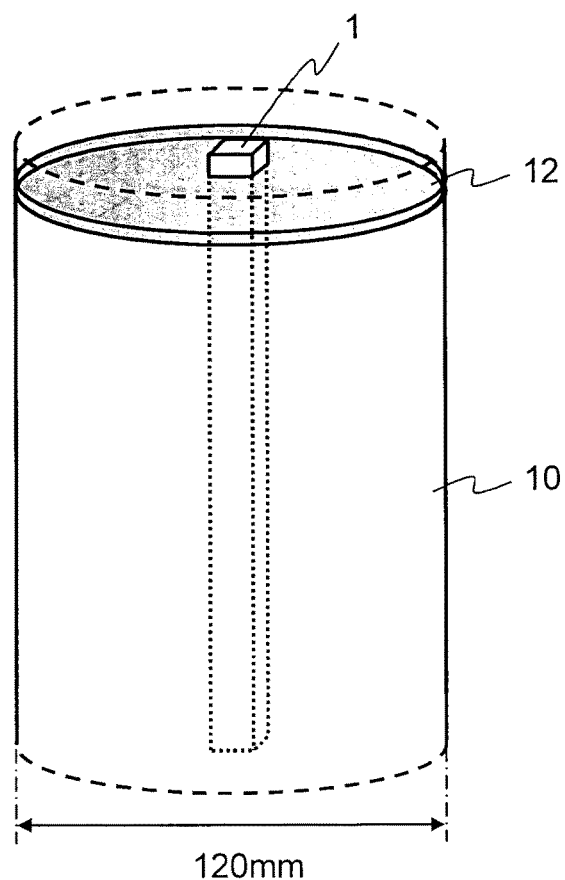
FIG. 1C is a diagram for illustrating another example of the sampling of a plate-like sample for use in an X-ray diffraction measurement from a polycrystalline silicon rod grown by the deposition using a chemical vapor deposition method.
Figure 1D:
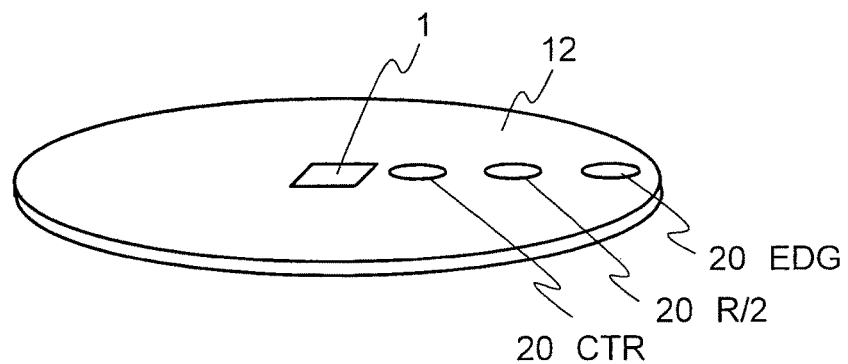
FIG. 1D is still a diagram for illustrating another example of the sampling of a plate-like sample for use in an X-ray diffraction measurement from a polycrystalline silicon rod grown by the deposition using a chemical vapor deposition method.

As shown in FIG. 1C, a plate-like sample 12 of nearly 2 mm in thickness, having a principal plane thereof perpendicular to the long axis direction of the polycrystalline silicon rod 10 is sampled, and the plate-like samples 20 of nearly 10 mm in diameter may also be sampled respectively from the portion (CTR) close to the silicon core wire 1, the portion (EDG) close to the side surface of the polycrystalline silicon rod 10 and the portion (R/2) midway between the CTR and the EGD of the plate-like sample 12 (FIG. 1D).

The diameter of the plate-like sample 20 of nearly 10 mm is just an illustrative example, and the diameter may be appropriately determined within a range causing no troubles in the X-ray diffraction measurement.

Figure 2:
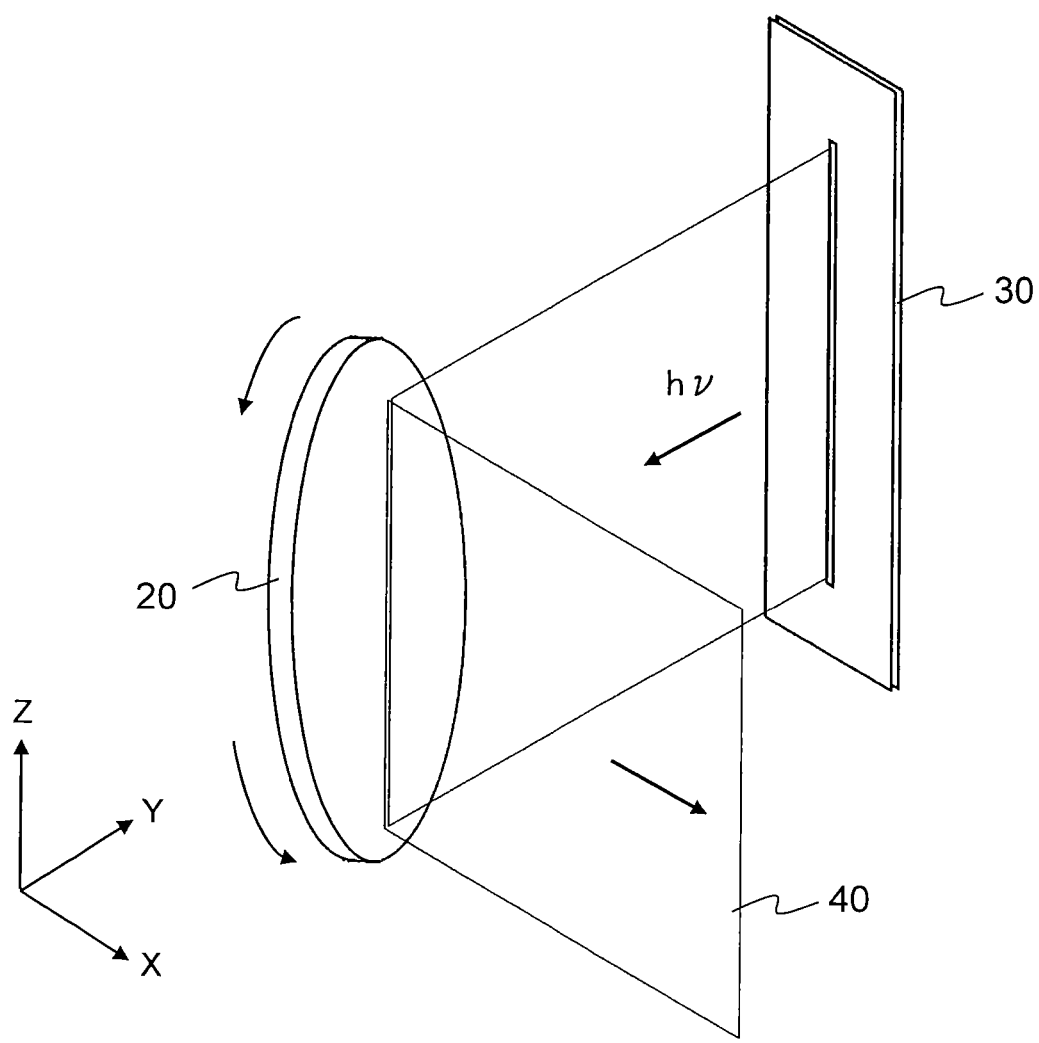
FIG. 2 is a diagram for illustrating the measurement of the X-ray diffraction from the plate-like sample sampled from a polycrystalline silicon rod.

FIG. 2 is a diagram for illustrating the measurement of the X-ray diffraction from the plate-like sample 20 thus sampled. The X-ray beam 40 emitted from the slit 30 to be collimated is made incident on the plate-like sample 20, the intensity of the diffracted X-ray beam for every sample rotation angle (θ) in the XY-plane is detected by the detector (not shown) and thus an X-ray diffraction chart is obtained.

Such a profile measurement is performed by rotating with small rotational intervals the plate-like sample 20 in the YZ-plane, and a profile is obtained at every rotation angle (ϕ) in the YZ-plane. The below-described evaluation of the non-orientation property is performed on the basis of the radar chart obtained from the X-ray diffraction measurement carried out by rotating the plate-like sample 20 by 360 degrees in the YZ-plane, namely, the X-ray diffraction measurement carried out omnidirectionally (ϕ=0° to 360°) in the plane of the plate-like sample 20.

Figure 3:
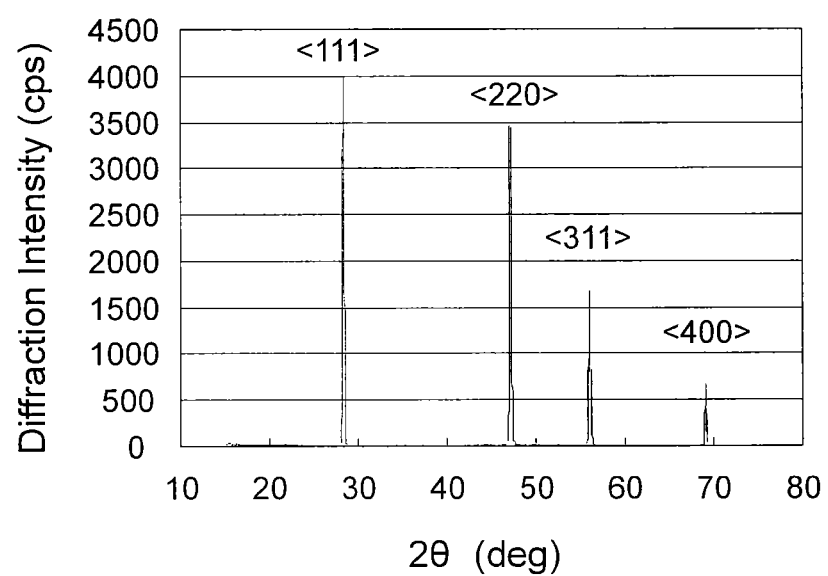
FIG. 3 is an example of the X-ray diffraction chart of a sample as a powder prepared by pulverizing polycrystalline silicon.

As described above, a sample prepared as a powder by pulverizing polycrystalline silicon can be handled as being perfectly randomly oriented, the X-ray diffraction chart obtained from such a powder sample comes to be a chart such as the chart shown in FIG. 3, and the chart is not substantially changed by rotating the sample by any angle in relation to the incident X-ray. The radar chart obtained by plotting the dependence of the diffraction intensity on the rotation angle ϕ comes to be a nearly perfect circle for any one of the Miller plane indices.

The present inventors use the "circularity" of such a radar chart as a reference of the non-orientation property; the case showing no peaks deviating from the average value ±2×standard deviation ($\mu \pm 2\sigma$), to include 95% of the total data of the diffraction intensity, is defined as "non-oriented," and the case showing peaks deviating from $\mu \pm 2\sigma$ is evaluated as "oriented."

According to the evaluation, performed by the present inventors, of a large number of the polycrystalline silicon rods different from each other in the production conditions, depending on the conditions such as the deposition conditions, differences are found in the degree of the orientation in terms of the above-described meaning; alternatively, it has been revealed that even in one and the same polycrystalline silicon rod, the portions close to the silicon core wire and the portions close to the side surface of the polycrystalline silicon rod are sometimes found to be different in the degree of the orientation. Within the range investigated by the present inventors, in the case of the "orientated" polycrystalline silicon rod, the samples sampled from the portions closer to the side surface of the polycrystalline silicon rod tend to have higher orientation property.

Accordingly, in the present invention, for the purpose of stably performing the production of single-crystalline silicon by using a non-oriented polycrystalline silicon raw material, plate-like samples each having as a principal plane thereof a cross section perpendicular to the long axis direction of a polycrystalline silicon rod grown by the deposition using a chemical vapor deposition method are sampled; an X-ray diffraction measurement is performed omnidirectionally in the plane of each of the plate-like samples thus samples; and when none of the plate-like samples has any X-ray diffraction peak with a diffraction intensity deviating from the average value ±2×standard deviation ($\mu \pm 2\sigma$) for any one of the Miller indices <111>, <220>, <311> and <400>, the polycrystalline silicon rod is selected as the raw material for use in the production of single-crystalline silicon. For example, in the case where the plate-like samples 20 are sampled from three portions by the sampling method shown in FIG. 1C and FIG. 1D, an X-ray diffraction measurement is performed omnidirectionally in the plane for each of all these three plate-like samples 20 CTR, 20 R/2 and 20 EDG, and when none of the samples does not satisfy the foregoing evaluation standard, the polycrystalline silicon rod is selected as the raw material for use in the production of single-crystalline silicon.

The polycrystalline silicon rod thus selected or the polycrystalline silicon block obtained by pulverizing the polycrystalline silicon rod thus selected for any one of the Miller indices <111>, <220>, <311> and <400> is polycrystalline silicon having an orientation property such that no X-ray diffraction peak having a diffraction intensity deviating from the average value ±2×standard deviation ($\mu \pm 2\sigma$) is shown; and in the method for producing single-crystalline silicon according to the present invention, the polycrystalline silicon rod thus selected or the polycrystalline silicon block obtained by pulverizing the polycrystalline silicon rod thus selected is used as a raw material for use in the production of single-crystalline silicon.

The crystal growth performed by the FZ method with the non-oriented polycrystalline silicon rod, or the crystal growth performed by the CZ method with the non-oriented polycrystalline silicon block obtained by crushing the non-oriented polycrystalline silicon rod suppresses the local occurrence of the portions remaining unmelted, and can contribute to the stable production of single-crystalline silicon.

EXAMPLE

Table 1 collectively shows the results of counting the X-ray diffraction peaks deviating from the average value ±2×standard deviation ($\mu \pm 2\sigma$) for each of the Miller indices <111>, <220>, <311> and <400> for each of the eight polycrystalline silicon rods grown by the deposition using a chemical vapor deposition method, wherein for each of the eight rods, the radar chart prepared according to the foregoing procedure for the 20 CTR of the three plate-like samples sampled by the method shown in FIG. 1C and FIG. 1D was used for the counting. The case where no deviating X-ray diffraction peak was found was evaluated as non-oriented. For the other two plate-like samples 20 R/2 and 20 EDG of the three plate-like samples sampled, the radar charts were prepared by the same procedures as described above and the non-orientation property was evaluated; however, the results thus obtained were the same as those shown in Table 1 and hence are omitted.

TABLE 1

| Sample | <111> | <220> | <311> | <400> |
|--------|-------|-------|-------|-------|
| A | 0 | 0 | 0 | 0 |
| B | 0 | 0 | 0 | 0 |
| C | 0 | 0 | 0 | 0 |
| D | 0 | 0 | 0 | 0 |
| E | 0 | 0 | 0 | 0 |
| f | 1 | 0 | 0 | 1 |
| g | 1 | 0 | 0 | 0 |
| h | 0 | 0 | 0 | 1 |

Figure 4A:
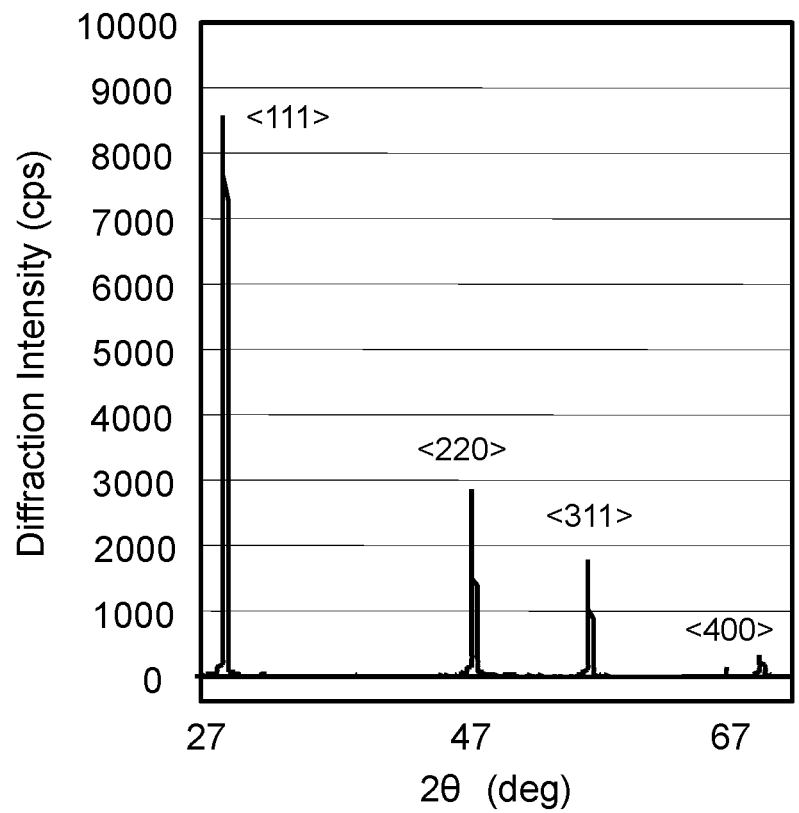
FIG. 4A is an example of the X-ray diffraction chart obtained from the sample A.
Figure 4B:
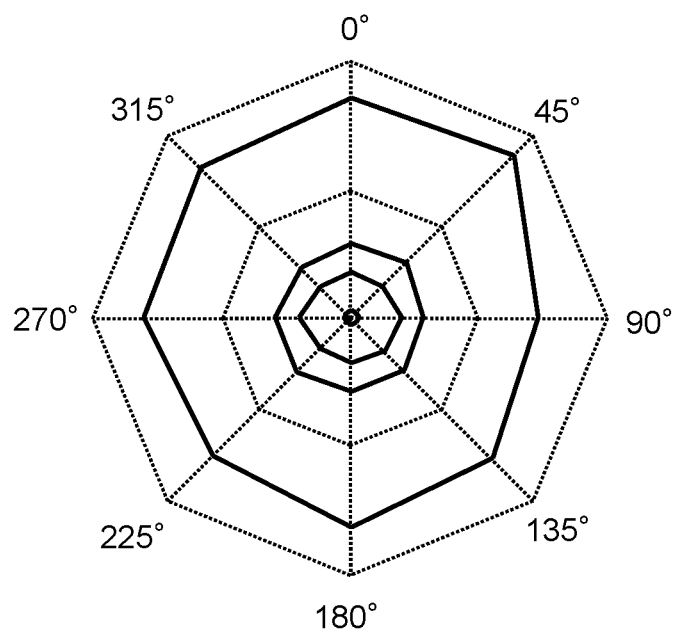
FIG. 4B is a radar chart prepared from the rotation angle $\phi$ and the diffraction intensity cps of the sample A.

FIG. 4A is an example of the X-ray diffraction profile obtained from the sample A (namely, the plate-like sample 20 CTR sampled from the polycrystalline silicon rod A), and FIG. 4B is the radar chart prepared from the rotation angles φ and the diffraction intensities cps of the sample A. The diffraction intensity from the lattice plane of any one of the Miller indices <111>, <220>, <311> and <400> of the sample A shows a shape close to a perfect circle, and for any one of the Miller indices <111>, <220>, <311> and <400>, no X-ray diffraction peak deviating from the average value ±2×standard deviation (μ±2σ) was not found to appear.

Figure 5A:
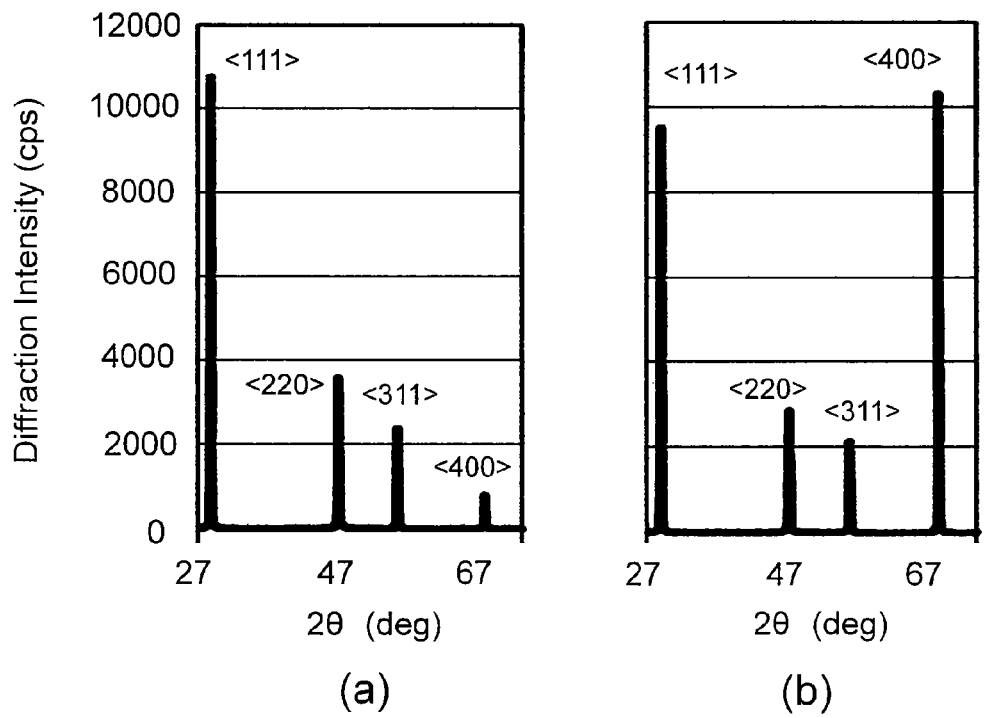
FIG. 5A is an example of the X-ray diffraction chart obtained from the sample h: (a) $\phi = 0°$ and (b) $\phi = 45°$.
Figure 5B:
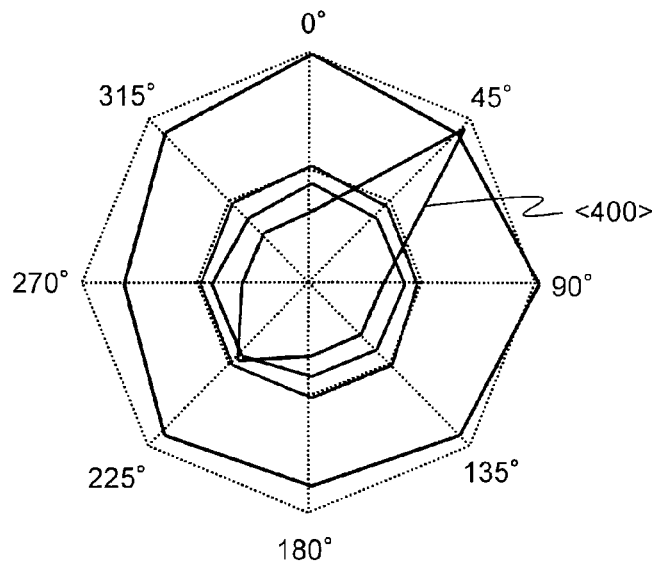
FIG. 5B is a radar chart prepared from the rotation angle $\phi$ and the diffraction intensity cps of the sample h.

FIG. 5A is an example of the X-ray diffraction profile obtained from the sample h (namely, the plate-like sample 20 CTR sampled from the polycrystalline silicon rod h), wherein (a) corresponds to φ=0° and (b) corresponds to φ=45°. FIG. 5B is the radar chart prepared from the rotation angles φ and the diffraction intensities cps of the sample h. The diffraction intensity from the lattice plane of any one of the Miller indices <111>, <220>, <311> and <400> of the sample h shows a shape close to a perfect circle, and for any one of the Miller indices <111>, <220>, <311> and <400>, no X-ray diffraction peak deviating from the average value ±2×standard deviation (μ±2σ) was not found to appear.

However, the diffraction intensity from the lattice plane of the Miller index <400> shows an extremely distorted shape, and in the profile measured at a rotation angle of φ=45°, an X-ray diffraction peak largely deviating from the average value ±2×standard deviation (μ±2σ) was found to appear.

Figure 6A:
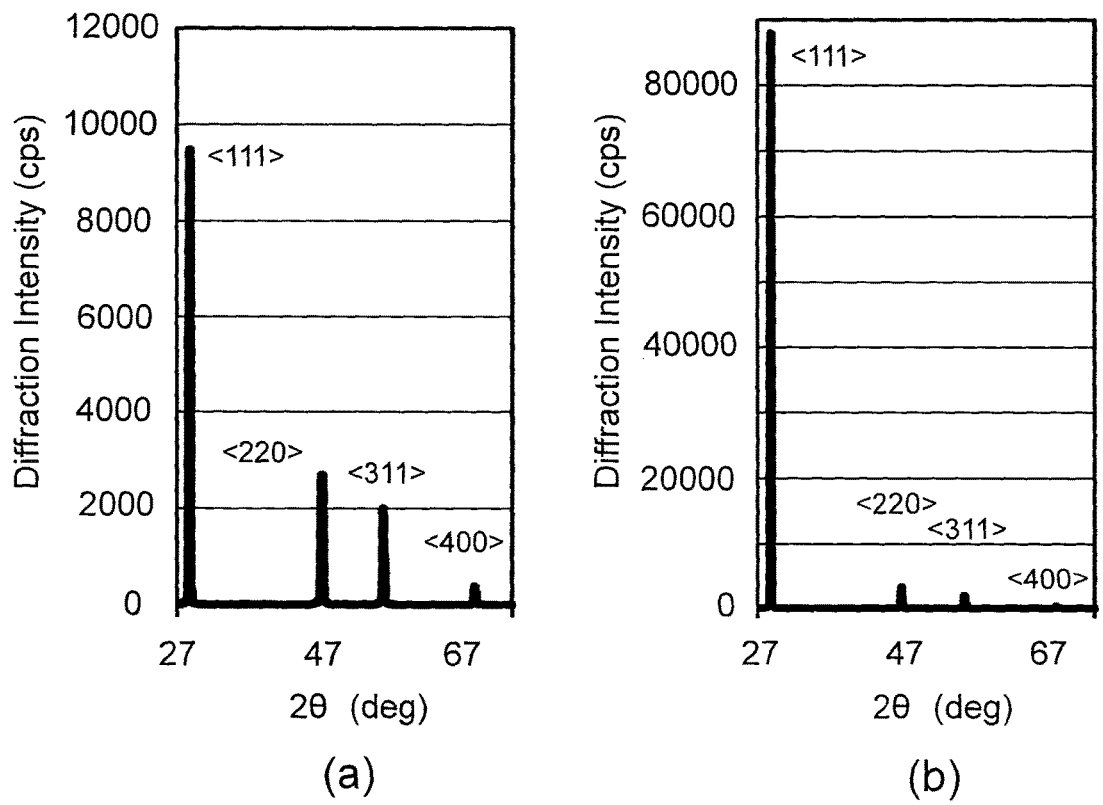
FIG. 6A is an example of the X-ray diffraction chart obtained from the sample g: (a) $\phi = 0°$ and (b) $\phi = 270°$.
Figure 6B:
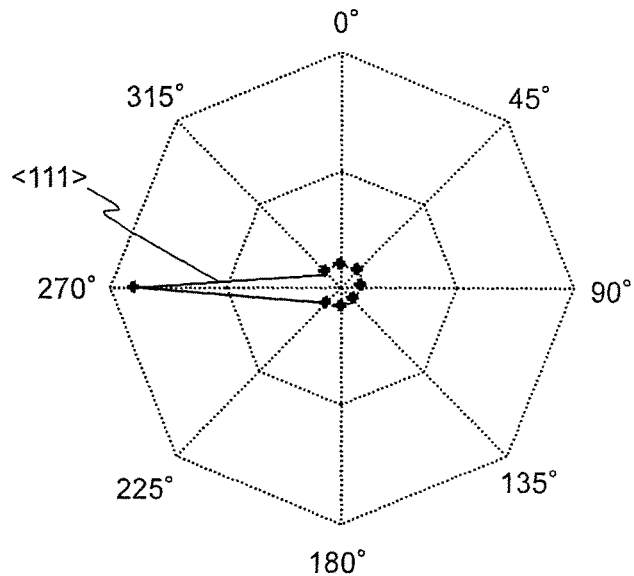
FIG. 6B is a radar chart prepared from the rotation angle $\phi$ and the diffraction intensity cps from the lattice plane having a Miller index of <111>.

FIG. 6A is an example of the X-ray diffraction profile obtained from the sample g (namely, the plate-like sample 20 CTR sampled from the polycrystalline silicon rod g), wherein (a) corresponds to φ=0° and (b) corresponds to φ=270°. FIG. 6B is the radar chart prepared from the rotation angles φ and the diffraction intensities cps of the sample g. Although the presentation of the radar chart was omitted, the diffraction intensity from the lattice plane of any one of the Miller indices <400>, <220> and <311> of the sample g shows a shape close to a perfect circle, and for any one of the Miller indices <400>, <220> and <311>, no X-ray diffraction peak deviating from the average value ±2×standard deviation (μ±2σ) was not found to appear.

However, the diffraction intensity from the lattice plane of the Miller index <111> shows an extremely distorted shape, and in the profile measured at a rotation angle of φ=270°, an X-ray diffraction peak largely deviating from the average value ±2×standard deviation (μ±2σ) was found to appear.

According to such a procedure as described above, the "non-oriented" polycrystalline silicon rods (Example) and the "oriented" polycrystalline silicon rods (Comparative Example) were classified, and the preparation experiments of the single-crystalline ingots were performed with the FZ method by using as the raw materials the respective polycrystalline silicon rods, and the occurrence/non-occurrence of the extinguishment of the crystal line was examined. The three polycrystalline silicon rods (non-oriented products) of Example and the three polycrystalline silicon rods (oriented products) of Comparative Example were used and the crystal growth conditions other than crystal growth conditions of the polycrystalline silicon rods were designed to be the same. The results thus obtained are collected in Table 2.

TABLE 2

|  | First rod | Second rod | Third rod |
| --- | --- | --- | --- |
| Non-oriented product | No extinguishment of crystal line | No extinguishment of crystal line | No extinguishment of crystal line |
| Oriented product | Extinguishment of crystal line | Extinguishment of crystal line | Extinguishment of crystal line |

TABLE 2-continued

|  | First rod | Second rod | Third rod |
| --- | --- | --- | --- |

As can be clearly seen from the above-described results, the use of the polycrystalline silicon materials high in random orientation property, namely, the non-oriented polycrystalline silicon materials allows the rate of becoming free from dislocation to be 100% and thus allows single-crystalline silicon to be stably produced.

INDUSTRIAL APPLICABILITY

The present invention contributes to the stable production of single-crystalline silicon.

REFERENCE SIGNS LIST

1 Silicon core wire
10 Polycrystalline silicon rod
11 Rod
12, 20 Plate-like samples
30 Slit
40 X-ray beam

The invention claimed is:

1. A method for selecting a polycrystalline silicon rod, the method comprising:
   obtaining one or more plate-like samples from a polycrystalline silicon rod grown by a chemical vapor deposition process, each of the one or more plate-like samples having a cross section perpendicular to a long axis direction of the polycrystalline silicon rod, wherein the cross section is a principal plane of each of the one or more plate-like samples;
   performing an X-ray diffraction measurement omnidirectionally in the principal plane of each of the one or more plate-like samples; and
   selecting the polycrystalline silicon rod as suitable for use in the production of single-crystalline silicon when none of the plate-like samples has any X-ray diffraction peak with a diffraction intensity deviating from an average value ±2×standard deviation found for any one of the Miller indices <111>, <220>, <311> and <400>.

2. The method according to claim 1, wherein the polycrystalline silicon rod is a polycrystalline silicon rod grown by a Siemens method.

3. A method for producing single-crystalline silicon, the method comprising crushing the polycrystalline silicon rod selected by the method according to claim 2.

4. A method for producing a polycrystalline silicon block, the method comprising crushing the polycrystalline silicon rod selected by the method according to claim 2.

5. A method for producing single-crystalline silicon, the method comprising crushing the polycrystalline silicon block obtained by the method according to claim 4.

6. A method for producing single-crystalline silicon, the method comprising crushing the polycrystalline silicon rod selected by the method according to claim 1.

7. A method for producing a polycrystalline silicon block, the method comprising crushing the polycrystalline silicon rod selected by the method according to claim 1.

8. A method for producing single-crystalline silicon, the method comprising crushing the polycrystalline silicon block obtained by the method according to claim 7.

* * * * *